US00PP21906P2

(12) United States Plant Patent
Zaiger et al.

(10) Patent No.: US PP21,906 P2
(45) Date of Patent: May 10, 2011

(54) CHERRY TREE NAMED 'ROYAL MARIE'

(50) Latin Name: *Prunus avium*
Varietal Denomination: Royal Marie

(76) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 12/655,176

(22) Filed: Dec. 24, 2009

(51) Int. Cl.
*A01H 5/00* (2006.01)

(52) U.S. Cl. ..... Plt./181

(58) Field of Classification Search ..... Plt./181
See application file for complete search history.

*Primary Examiner* — Susan B McCormick Ewoldt

(57) ABSTRACT

A new and distinct variety of cherry tree (*Prunus avium*). The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Vigorous and upright tree growth.
2. Early blooming with a low winter chilling requirement of approximately 500 hours at or below 45° F.
3. Regular and productive bearer of large size fruit.
4. Fruit maturing in the early season.
5. Fruit with an attractive red skin color.
6. Fruit with good flavor and eating quality.

1 Drawing Sheet

Botanical classification: *Prunus avium.*

BACKGROUND OF THE VARIETY

1. Field of the Invention

In the field of plant genetics, we conduct an extensive and continuing plant-breeding program including the organization and asexual reproduction of orchard trees and of which; plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

2. Prior Varieties

Among the existing varieties of cherry trees which are known to us and mentioned herein, 'Minnie Royal' (U.S. Plant Pat. No. 12,942) and 'Bing' cherry (non-patented).

STATEMENT REGARDING FEDERALLY SPONSORED RESEARCH AND DEVELOPMENT

Not applicable.

ORIGIN OF THE VARIETY

The present new variety of cherry tree (*Prunus avium*) was originated by us in our experimental orchard located near Modesto, Calif. as an open pollinated seedling from a proprietary seedling selection with the field identification number '21ZC114'. The seed parent (21ZC114) is a second generation seedling from the cross of a selected proprietary seedling from an open pollinated 'Bing' Cherry (non-patented) and 'Minnie Royal' Cherry (U.S. Plant Pat. No. 12,942). A large group of these open pollinated seedlings were budded on to older trees of 'Mahaleb' Rootstock (non-patented) to accelerate earlier fruit production for evaluation. Under close and careful observation, one such seedling exhibited desirable fruit and tree characteristics and was selected in 2004 for additional asexual propagation and commercialization.

ASEXUAL REPRODUCTION OF THE VARIETY

Additional asexual reproduction of the new and distinct variety of cherry tree was by budding to 'Mahaleb' Rootstock (non-patented), as performed by us in our experimental orchard located near Modesto, Calif., and shows that reproductions true to the original tree and all characteristics of the tree and its fruit are established and transmitted through succeeding asexual propagations.

SUMMARY OF THE NEW VARIETY

The new and distinct cherry tree is of large size, vigorous upright growth and has a low winter chilling requirement of approximately 500 hours at or below 45° F. The tree is a regular and productive bearer of large size, early maturing fruit with good flavor and eating quality. The fruit is further characterized by its attractive red skin color, firm flesh, good handling and storage quality. In comparison to its seed parent '21ZC114', the fruit is larger in size and is 14 days earlier in maturity. In comparison to 'Minnie Royal' Cherry (U.S. Plant Pat. No. 12,942) the fruit is larger in size. In comparison to its ancestor 'Bing' Cherry (non-patented) the new variety has a lower chilling requirement, blooms 10 days earlier and the fruit matures 23 days earlier.

PHOTOGRAPH OF THE VARIETY

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 5 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 5 year old specimens grown near Modesto, Calif., with color in accordance with Munsell Book of Color.

Tree:

*Size.*—Large, pruned to 3.0 to 3.5 meters in height and width for economical harvesting of fruit.

*Vigor.*—Vigorous, tree growth of 1.5 to 2 meters in height the first growing season. Growth rate will vary with types of soil, fertility and cultural practices.

*Form.*—Upright, usually pruned to vase shape.

*Branching habit.*—Upright, crotch angle approximately 30°, increases with heavy crop load.

*Productivity.*—Productive, produces adequate set annually.

*Bearer.*—Regular. Has adequate fruit set annually. Set varies with climatic conditions at bloom time.

*Fertility.*—Self-sterile, pollinator required.

*Density.*—Medium dense, controlled by pruning.

*Hardiness.*—Tree grown in USDA Hardiness Zone 9. Hardy in all stone fruit growing areas of California. Winter chilling requirement approximately 500 hours at or below 45° F.

Trunk:

*Size.*—Large. Average circumference of 30.5 cm at 20.3 cm above ground on a 5 year old tree.

*Stocky.*—Medium stocky.

*Texture.*—Medium rough, roughness increases with age.

*Color.*—Varies from 5YR 2/4 to 7.5YR 3/2.

Branches:

*Size.*—Medium stocky. Average circumference 12.7 cm at 1.2 meters above ground. Crotch angle approximately 30°, increases with heavy crop load.

*Surface texture.*—New growth relatively smooth. Old growth medium rough, roughness increases with age of growth.

*Lenticels.*—Average 17 in a 25.8 sq cm area of branch. Average length 6.0 mm. Average width 2.0 mm. Color varies from 10YR 6/8 to 10YR 6/10.

*Color.*—New growth varies from 2.5GY 5/8 to 5GY 5/8. Old growth varies from 7.5YR 2/2 to 10YR 3/4, varies with age of growth.

Leaves:

*Size.*—Large. Average length 135.8 mm. Average width 68.1 mm.

*Form.*—Elliptic.

*Apex.*—Acuminate.

*Base.*—Cuneate.

*Margin.*—Doubly cerate.

*Thickness.*—Medium thick.

*Surface texture.*—Upper surface relatively smooth, slight indentations over midrib and leaf veins, glabrous. Lower surface relatively smooth, small ridges created by midrib and pinnate venation, glabrous.

*Petiole.*—Average length 33.4 mm. Average width 1.9 mm. Color varies from 5R 2/4 to 7.5R 2/6. Longitudinal groove, very shallow, glabrous.

*Glands.*—Reniform. Size — large. Average length 2.5 mm. Average width 1.8 mm. Located primarily on the upper portion of the petiole. Color varies from 7.5R 4/8 to 7.5Y 6/6.

*Stipules.*—Average number at base of leaf petiole — 2. Margin — pectinate. Color varies from 5R 3/4 to 7.5Y 4/6.

*Color.*—Upper surface varies from 5GY 4/8 to 5GY 3/6. Lower surface varies from 5GY 5/4 to 5GY 4/6. Midvein color varies from 10Y 5/4 to 10R 3/4.

Flower buds:

*Size.*—Large. Average length 16.8 mm. Average diameter 9.2 mm.

*Hardiness.*—Hardy with respect to California winters.

*Form.*—Conical, becoming elongated before opening.

*Pedicel.*—Average length 10.4 mm. Average width 1.2 mm. Color varies from 2.5GY 5/8 to 5GY 5/8.

*Color.*—N9.5/ (white), edged with 7.5RP 5/2 to 7.5RP 5/6 along upper surface of petals, color fades to white as buds open.

*Number of buds per spur.*—Average 5, varies from 4 to 6.

Flowers:

*Blooming period.*—Date of First Bloom Feb. 27, 2009. Date of Petal Fall Mar. 10, 2009, varies slightly with climatic conditions.

*Size.*—Large. Average height 20.7 mm. Average diameter 32.9 mm.

*Petals.*—Normally 5, varies from 5 to 6, alternately arranged to sepals. Size — large. Average length 17.7 mm. Average width 17.9 mm. Form — orbicular. Margin — sinuate. Color — N9.5/ (white). Both surfaces glabrous.

*Sepals.*—Normally 5, varies from 5 to 6, alternately arranged to petals. Size — large. Average length 7.7 mm. Average width 5.4 mm. Shape — triangular. Margin — entire. Color — upper surface varies from 5GY 6/6 to 5GY 5/6. Lower surface varies from 5GY 4/6 to 5R 3/6. Both surfaces glabrous.

*Stamens.*—Average number per flower 35. Average filament length 14.0 mm. Filament color N9.5/ (white). Anther color varies from 2.5Y 8.5/12 to 5Y 8/10.

*Pollen.*—Present, self sterile, pollinator required. Color varies from 2.5Y 7/10 to 2.5Y 7/12.

*Pistil.*—Normally 1. Average length 16.0 mm. Surface — glabrous. Position of stigma approximately 1.9 mm below anthers. Color varies from 10Y 7/8 to 2.5GY 7/6.

*Fragrance.*—Slight aroma.

*Color.*—N9.5/ (white).

*Number flowers per flower bud.*—Average 3, varies from 1 to 4.

*Pedicel.*—Average length 15.2 mm. Average width 1.3 mm. Color varies from 2.5GY 5/8 to 5GY 5/8.

Fruit:

*Maturity when described.*—Firm ripe.

*Date of first picking.*—Apr. 30, 2009.

*Date of last picking.*—May 9, 2009, varies slightly with climatic conditions.

*Size.*—Large. Average diameter axially 28.5 mm. Average transversely in suture plane 27.8 mm. Average weight 13.9 grams, varies slightly with fertility of the soil, amount of thinning and climatic conditions.

*Form.*—Globose, slightly flattened at apex and base.

*Suture.*—Nearly smooth to slightly lipped, extends from base to apex.

*Ventral surface.*—Nearly smooth to slightly lipped.
*Apex.*—Rounded to slightly retuse.
*Base.*—Retuse.
*Stem cavity.*—Rounded to slightly elongated in suture plane. Average depth 1.1 mm. Average diameter 4.8 mm.

Stem:
*Size.*—Large. Average length 42.0 mm. Average diameter 1.5 mm.
*Color.*—Varies from 5GY 5/6 to 5GY 4/6.

Flesh:
*Ripens.*—Even to slightly earlier at the apex.
*Texture.*—Very firm.
*Fibers.*—Few, small, tender.
*Firmness.*—Very firm.
*Aroma.*—Moderate.
*Amydgalin.*—Undetected.
*Eating quality.*—Very good.
*Flavor.*—Good, good balance between acid and sugar.
*Juice.*—Moderate amount, enhances flavor.
*Brix.*—Average Brix 15.8°, varies slightly with amount of fruit per tree and climatic conditions.
*Color.*—Varies from 7.5Y 9/2 to 7.5R 3/10. Pit cavity color varies from 7.5R 3/10 to 7.5R 2/8.

Skin:
*Thickness.*—Medium.
*Surface.*—Smooth.
*Bloom.*—Wanting.
*Tendency to crack.*—None during dry weather, slight tendency to crack during wet weather, varies with stage of maturity.
Color.—Varies from 7.5R 2/4 to 7.5R 3/10.
*Tenacity.*—Tenacious to flesh.
*Astringency.*—Undetected.

Stone:
*Type.*—Clingstone.
*Size.*—Medium. Average length 11.3 mm. Average width 10.5 mm. Average thickness 8.3 mm.
*Form.*—Ovoid.
*Base.*—Flat to slightly rounded.
*Apex.*—Slight apical point. Average length 0.2 mm.
*Surface.*—Smooth to slightly pitted throughout.
*Sides.*—Varies from equal to unequal with one side extending further from the suture plane.
*Ridges.*—Small ridges running along each side of the suture.
*Tendency to split.*—None.
*Color.*—Varies from 10YR 6/6 to 2.5Y 6/6 when dry.

Kernel:
*Size.*—Medium. Average length 7.7 mm. Average width 5.6 mm. Average thickness 4.3 mm.
*Form.*—Ovoid.
*Viability.*—Partially viable, incomplete embryos in some stones.
*Skin color.*—Varies from 2.5Y 8.5/4 to 5Y 8/4, when dry.

Use:
*Dessert.*—Market — local and long distance.

Keeping quality: Good, held firm in cold storage 2 weeks at 38° to 42° F. without breakdown of flesh, shriveling or appreciable loss of flavor.

Shipping quality: Good, showed minimal flesh bruising or skin scarring during picking and packing trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

I claim:

1. A new and distinct variety of cherry tree, substantially as illustrated and described.

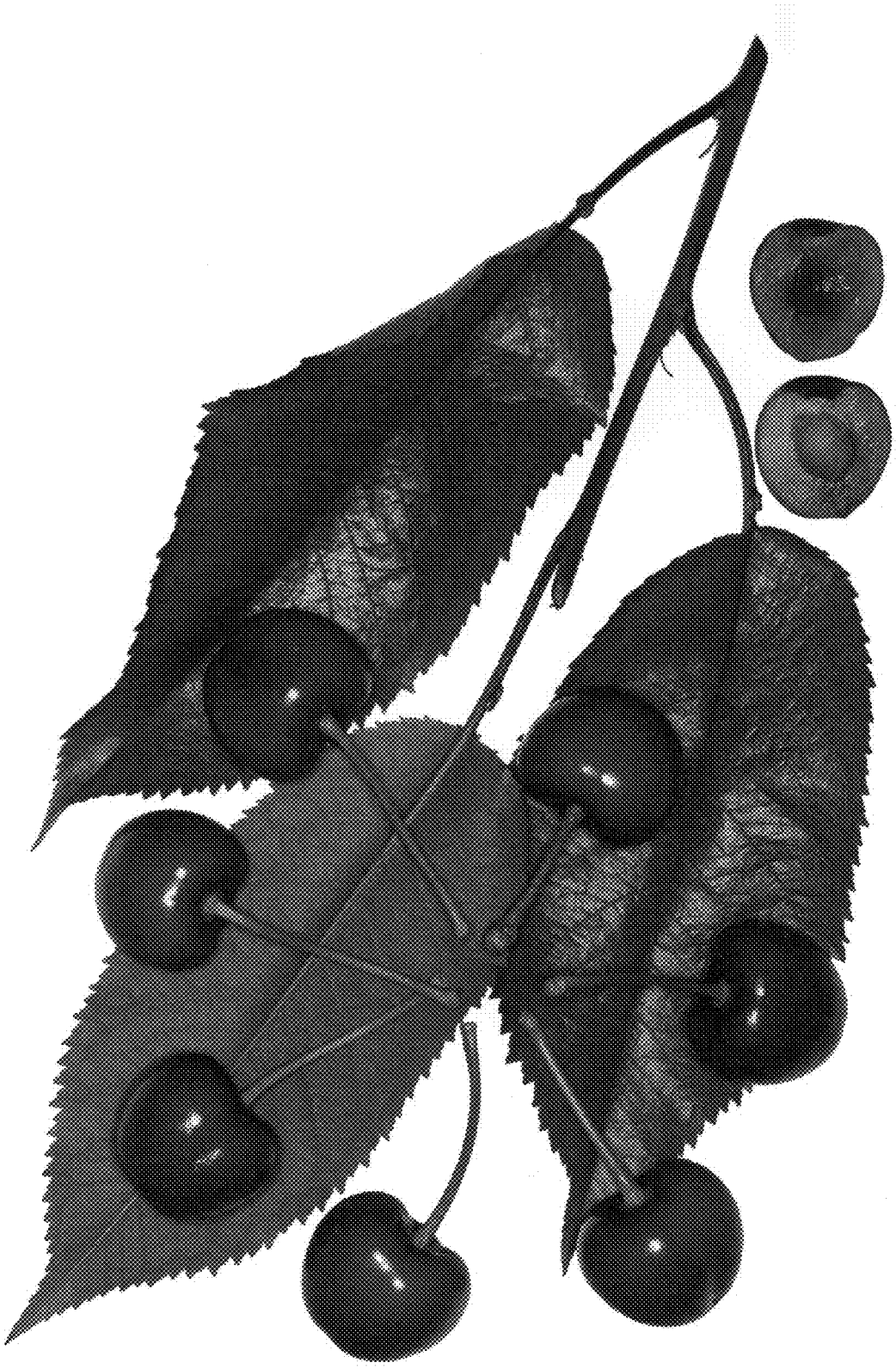

* * * * *